United States Patent
Root et al.

(10) Patent No.: US 10,391,282 B2
(45) Date of Patent: Aug. 27, 2019

(54) GUIDEWIRES AND METHODS FOR PERCUTANEOUS OCCLUSION CROSSING

(71) Applicant: Teleflex Innovations S.à.r.l., Luxembourg (LU)

(72) Inventors: Howard C. Root, Excelsior, MN (US); John Bridgeman, Minneapolis, MN (US)

(73) Assignee: Teleflex Innovations S.à.r.l., Luxembourg (LU)

( * ) Notice: Subject to any disclaimer, the term of this patent is extended or adjusted under 35 U.S.C. 154(b) by 714 days.

(21) Appl. No.: 14/697,819

(22) Filed: Apr. 28, 2015

(65) Prior Publication Data

US 2016/0008584 A1   Jan. 14, 2016

Related U.S. Application Data

(60) Provisional application No. 62/022,024, filed on Jul. 8, 2014.

(51) Int. Cl.
*A61M 25/09* (2006.01)
*A61M 25/01* (2006.01)

(52) U.S. Cl.
CPC ..... *A61M 25/09* (2013.01); *A61M 2025/0197* (2013.01); *A61M 2025/09083* (2013.01);
(Continued)

(58) Field of Classification Search
CPC ........ A61M 25/09; A61M 2025/09166; A61M 2025/09133; A61M 2025/0197;
(Continued)

(56) References Cited

U.S. PATENT DOCUMENTS 3,452,742 A   7/1969  Muller
4,846,186 A   7/1989  Box et al.
(Continued)

FOREIGN PATENT DOCUMENTS

EP   0468645 A1   1/1992
EP   0495299 A1   7/1992
(Continued)

OTHER PUBLICATIONS

Scholtes, Vincent P.W. et al. "Subintimal Angioplasty Track of the Superficial Femoral Artery: A Histological Analysis," Circulation: Cardiovascular Interventions, published by American Heart Association, Dallas, TX, p. e6-e8 (Feb. 2012).
(Continued)

*Primary Examiner* — Adam J Eiseman
(74) *Attorney, Agent, or Firm* — Gregory W. Smock

(57) ABSTRACT

Guidewires and related methods for percutaneous crossing of an occlusion in a blood vessel are disclosed. A guidewire can include a core member and a jacket member. The core member can extend from a proximal end portion to a distal end portion, with the distal end portion including a first segment, a more distal second segment and a more proximal third segment. The first segment can be configured to encourage prolapse by way of a short taper or a diameter-reduced portion. The jacket member can surround at least the distal end portion of the core member. A method can include advancing a distal end portion of the guidewire through the natural lumen of a blood vessel to a location near an occlusion. A longitudinal pushing force can be applied to a proximal end portion of the guidewire, thereby causing a first segment of the distal end portion to prolapse.

7 Claims, 9 Drawing Sheets

(52) U.S. Cl.
CPC ............ *A61M 2025/09133* (2013.01); *A61M 2025/09166* (2013.01)

(58) Field of Classification Search
CPC ......... A61M 2025/09175; A61M 2025/09183; A61M 25/09016; A61M 25/09025; A61M 25/09033
USPC ....................................................... 600/585
See application file for complete search history.

(56) References Cited

U.S. PATENT DOCUMENTS

| | | | |
|---|---|---|---|
| 5,303,714 A * | 4/1994 | Abele | A61B 17/22 600/585 |
| 5,385,152 A | 1/1995 | Abele et al. | |
| 5,505,699 A * | 4/1996 | Forman | A61M 25/104 128/898 |
| 5,728,122 A | 3/1998 | Leschinsky et al. | |
| 5,938,623 A | 8/1999 | Quiachon et al. | |
| RE37,148 E | 4/2001 | Shank | |
| 6,211,049 B1 | 4/2001 | Farrar | |
| 6,217,527 B1 | 4/2001 | Selmon et al. | |
| 6,231,546 B1 | 5/2001 | Milo et al. | |
| 6,235,000 B1 | 5/2001 | Milo et al. | |
| 6,254,550 B1 | 7/2001 | McNamara et al. | |
| 6,464,650 B2 | 10/2002 | Jafari et al. | |
| 6,500,130 B2 | 12/2002 | Kinsella et al. | |
| 6,511,458 B2 | 1/2003 | Milo et al. | |
| 6,514,217 B1 | 2/2003 | Selmon et al. | |
| 6,638,266 B2 | 10/2003 | Wilson et al. | |
| 6,719,725 B2 | 4/2004 | Milo et al. | |
| 6,761,696 B1 | 7/2004 | Wong | |
| 7,004,173 B2 | 2/2006 | Sparks et al. | |
| 7,128,718 B2 | 10/2006 | Hojeibane et al. | |
| 7,520,863 B2 | 4/2009 | Grewe et al. | |
| 7,715,903 B2 | 5/2010 | Hartley et al. | |
| 7,785,273 B2 | 8/2010 | Eskuri | |
| 7,785,274 B2 | 8/2010 | Mishima et al. | |
| 7,938,819 B2 | 5/2011 | Kugler et al. | |
| 7,942,832 B2 | 5/2011 | Kanuka et al. | |
| 8,022,331 B2 | 9/2011 | Reynolds et al. | |
| 8,083,727 B2 | 12/2011 | Kugler et al. | |
| 8,202,246 B2 | 6/2012 | Kugler et al. | |
| 8,226,566 B2 | 7/2012 | Nita | |
| 8,241,311 B2 | 8/2012 | Ward et al. | |
| 8,252,015 B2 | 8/2012 | Leeflang et al. | |
| 8,257,278 B2 | 9/2012 | Howland et al. | |
| 8,257,382 B2 | 9/2012 | Rottenberg et al. | |
| 8,257,383 B2 | 9/2012 | Rottenberg et al. | |
| 8,277,469 B2 * | 10/2012 | Carmeli | A61B 17/2202 600/585 |
| 8,313,445 B2 | 11/2012 | Mishima et al. | |
| 8,323,261 B2 | 12/2012 | Kugler et al. | |
| 8,337,425 B2 | 12/2012 | Olson et al. | |
| 8,374,680 B2 | 2/2013 | Thompson | |
| 8,376,961 B2 | 2/2013 | Layman et al. | |
| 8,512,310 B2 | 8/2013 | Kugler et al. | |
| 8,551,020 B2 | 10/2013 | Chen et al. | |
| 8,679,049 B2 | 3/2014 | Nita | |
| 8,721,675 B2 | 5/2014 | Rottenberg et al. | |
| 8,920,449 B2 | 12/2014 | Wilkinson | |
| 8,932,315 B2 | 1/2015 | Brian et al. | |
| 8,956,376 B2 | 2/2015 | Alvarez et al. | |
| 8,961,494 B2 | 2/2015 | Kugler et al. | |
| 8,998,936 B2 | 4/2015 | Alvarez et al. | |
| 9,060,802 B2 | 6/2015 | Kugler et al. | |
| 9,174,032 B2 | 11/2015 | Zhou et al. | |
| 9,272,121 B2 | 3/2016 | Piccagli | |
| 9,278,192 B2 | 3/2016 | Copeta et al. | |
| 9,301,774 B2 | 4/2016 | O'Day | |
| 9,308,019 B2 | 4/2016 | Kugler et al. | |
| 9,320,874 B2 | 4/2016 | Sina | |
| 9,402,646 B2 | 8/2016 | Nita | |
| 9,402,649 B2 | 8/2016 | Brian et al. | |
| 9,402,981 B2 | 8/2016 | Anderson | |
| 9,408,998 B2 | 8/2016 | Alvarez et al. | |
| 9,451,984 B2 | 9/2016 | Zhou et al. | |
| 9,486,239 B2 | 11/2016 | Anderson et al. | |
| 9,579,489 B2 | 2/2017 | Zhou et al. | |
| 9,603,615 B2 | 3/2017 | Sarge | |
| 9,717,889 B2 | 8/2017 | Kugler et al. | |
| 2002/0082523 A1 | 6/2002 | Kinsella et al. | |
| 2002/0183654 A1 | 12/2002 | Zhou | |
| 2004/0073141 A1 | 4/2004 | Hartley et al. | |
| 2004/0193151 A1 * | 9/2004 | To | A61B 18/1492 606/41 |
| 2004/0199088 A1 | 10/2004 | Bakos et al. | |
| 2007/0219464 A1 | 9/2007 | Davis et al. | |
| 2008/0004606 A1 | 1/2008 | Swain et al. | |
| 2008/0064988 A1 * | 3/2008 | Carter | A61M 25/09 600/585 |
| 2008/0228171 A1 | 9/2008 | Kugler et al. | |
| 2008/0269641 A1 | 10/2008 | Coyle | |
| 2010/0228151 A1 | 9/2010 | Carmeli et al. | |
| 2011/0098648 A1 | 4/2011 | Kato | |
| 2011/0276079 A1 | 11/2011 | Kugler et al. | |
| 2012/0095485 A1 | 4/2012 | Cully et al. | |
| 2012/0123329 A1 | 5/2012 | Kato | |
| 2012/0158021 A1 | 6/2012 | Morrill | |
| 2012/0239073 A1 * | 9/2012 | Hubregtse | A61B 17/00234 606/190 |
| 2012/0323251 A1 | 12/2012 | Kugler et al. | |
| 2013/0046286 A1 | 2/2013 | Simpson | |
| 2013/0110144 A1 | 5/2013 | Olson et al. | |
| 2013/0238003 A1 | 9/2013 | Fischer et al. | |
| 2013/0245430 A1 | 9/2013 | Selmon et al. | |
| 2013/0317534 A1 | 11/2013 | Zhou et al. | |
| 2014/0046216 A1 | 2/2014 | Palme et al. | |
| 2014/0121689 A1 | 5/2014 | Kugler et al. | |
| 2014/0275983 A1 | 9/2014 | Piccagli | |
| 2014/0277053 A1 | 9/2014 | Wang et al. | |
| 2014/0277068 A1 | 9/2014 | Kugler et al. | |
| 2014/0371718 A1 | 12/2014 | Alvarez et al. | |
| 2015/0051633 A1 * | 2/2015 | Sina | A61M 25/0074 606/194 |
| 2015/0080928 A1 | 3/2015 | Kugler et al. | |
| 2015/0148706 A1 * | 5/2015 | Abner | A61M 25/09 600/585 |
| 2015/0165163 A1 | 6/2015 | Alvarez et al. | |
| 2015/0320975 A1 | 11/2015 | Simpson et al. | |
| 2016/0045713 A1 | 2/2016 | Waisman et al. | |
| 2016/0074627 A1 | 3/2016 | Cottone | |
| 2016/0081709 A1 | 3/2016 | Majercak | |
| 2016/0157872 A1 | 6/2016 | Cage et al. | |
| 2016/0183953 A1 | 6/2016 | Kugler et al. | |
| 2016/0192952 A1 | 7/2016 | Warren | |
| 2016/0206334 A1 | 7/2016 | Rizk et al. | |
| 2016/0213386 A1 | 7/2016 | Wilkinson | |
| 2016/0235948 A1 | 8/2016 | Sina | |
| 2016/0250448 A1 | 9/2016 | Copeta et al. | |
| 2016/0271374 A1 | 9/2016 | Spencer | |
| 2016/0302807 A1 | 10/2016 | Anderson | |
| 2016/0317175 A1 | 11/2016 | Remmerswaal et al. | |
| 2016/0331567 A1 | 11/2016 | Nita | |
| 2016/0338721 A1 | 11/2016 | Alvarez et al. | |
| 2016/0361076 A1 | 12/2016 | Zhou et al. | |
| 2017/0020563 A1 | 1/2017 | Anderson et al. | |
| 2017/0079671 A1 | 3/2017 | Morero et al. | |
| 2017/0100141 A1 | 4/2017 | Morero et al. | |
| 2017/0128090 A1 | 5/2017 | Sarge | |
| 2017/0172653 A1 | 6/2017 | Urbanski et al. | |
| 2018/0000513 A1 | 1/2018 | Kugler et al. | |

FOREIGN PATENT DOCUMENTS

| | | |
|---|---|---|
| EP | 0778042 B1 | 3/2000 |
| EP | 1419794 B1 | 11/2009 |
| EP | 2700368 B1 | 2/2015 |
| EP | 2636381 B1 | 3/2018 |
| WO | 1998005376 A1 | 2/1998 |
| WO | 2002096492 A2 | 12/2002 |
| WO | 2004018031 A2 | 3/2004 |
| WO | 2006039217 A1 | 4/2006 |

(56) References Cited

FOREIGN PATENT DOCUMENTS

| WO | 2007121002 A1 | 10/2007 |
| WO | 2010087953 A1 | 8/2010 |
| WO | 2010092347 A1 | 8/2010 |
| WO | 2010115163 A9 | 7/2011 |

OTHER PUBLICATIONS

PCT International Search Report dated Feb. 5, 2019 in application No. PCT/US2018/055832.
PCT Written Opinion dated Feb. 5, 2019 in application No. PCT/US2018/055832.

* cited by examiner

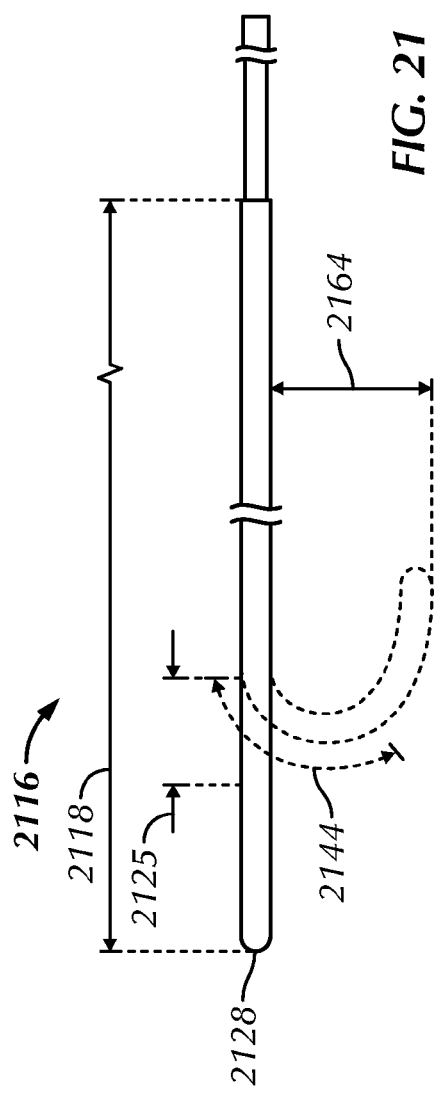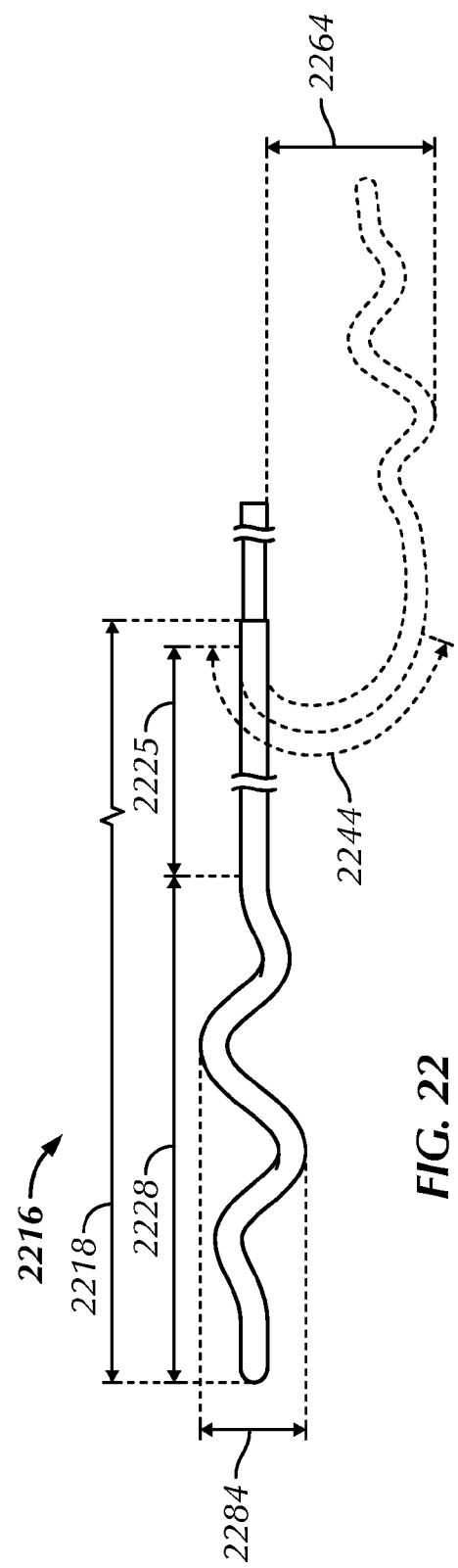

ance a guidewire from a location proximal of the occlusion to a location distal of the occlusion. In some instances, such as when the occlusive matter is soft or where the occlusion has a tiny opening, the guidewire can be forced through the occlusive matter and allowed to remain within the natural lumen of the blood vessel. In other instances, such as when the natural lumen of the blood vessel is totally occluded by hard plaque (e.g., calcified atherosclerotic plaque), the guidewire cannot cross the occlusion and, in response to a continued proximally-applied pushing force, may permanently kink and/or its distal end portion may deviate to an adjacent vessel wall and perforate the vessel.
GUIDEWIRES AND METHODS FOR PERCUTANEOUS OCCLUSION CROSSING

CLAIM OF PRIORITY

This non-provisional Patent application claims the benefit of priority under 35 U.S.C. § 119(e) to U.S. Provisional Patent Application Ser. No. 62/022,024, entitled "GUIDEWIRES AND METHODS FOR PERCUTANEOUS OCCLUSION CROSSING," filed on Jul. 8, 2014, which is herein incorporated by reference in its entirety.

TECHNICAL FIELD

This patent document relates to the field of minimally invasive catheterization. More particularly, but not by way of limitation, the patent document relates to devices and methods for percutaneous crossing of an occlusion in a blood vessel.

BACKGROUND

Heart attacks, strokes and other life-threatening events are caused by plaque build-up in blood vessels. Atherosclerotic plaque, for example, is known to build-up in arterial walls of the human body. This plaque build-up restricts circulation and can result in cardiovascular problems, particularly when the build-up occurs in coronary arteries.

A method for opening a partially occluded blood vessel is to guide one or more medical devices to a diseased (occlusion) site where they can be used to carry out treatment. A guidewire is often used for guiding a catheter or other treatment device toward the diseased site. The distal tip of the guidewire can be introduced into the body of a treated subject by means of a needle or other access device, which pierces the subject's skin, and advanced to the site. The catheter or other treatment device can then be threaded over the guidewire and advanced through internal blood vessel passages to the diseased site using the guidewire as a rail.

Total or near-total occlusions can block passage through portions of a blood vessel. In subjects suffering from a coronary chronic total occlusion (CTO), for example, successful treatment of the occlusion can be challenging. A factor that can determine whether a treating clinician can successfully treat the occlusion is the clinician's ability to advance a guidewire from a location proximal of the occlusion to a location distal of the occlusion. In some instances, such as when the occlusive matter is soft or where the occlusion has a tiny opening, the guidewire can be forced through the occlusive matter and allowed to remain within the natural lumen of the blood vessel. In other instances, such as when the natural lumen of the blood vessel is totally occluded by hard plaque (e.g., calcified atherosclerotic plaque), the guidewire cannot cross the occlusion and, in response to a continued proximally-applied pushing force, may permanently kink and/or its distal end portion may deviate to an adjacent vessel wall and perforate the vessel.

Overview

In use, a treating clinician handles a guidewire from its proximal end portion located outside the body of the treated subject; the treating clinician has limited control over the intermediate and distal end portions of the guidewire that are located within the natural lumen of a blood vessel.

The configuration and stiffness of the guidewire selected for a particular vessel occlusion can dictate whether or not the treatment will be successful. If a treating clinician selects a regular stiffness guidewire, passage through a CTO, for example, will likely be unsuccessful because the guidewire may kink or exhibit other plastic deformation when a strong pushing force is applied by the treating clinician. If the treating clinician selects a high stiffness guidewire, he/she may be able to pass through or around a CTO without the guidewire kinking but at the risk of vessel wall perforation (proximal or distal of the occlusion). For at least these reasons, treating clinicians oftentimes turn to bypass surgery as the preferred treatment for subjects with a CTO or near-total occlusion.

The present inventors recognize that less invasive passage of a guidewire through or around an occlusion is preferable to more invasive bypass surgery techniques. The inventors further recognize that specially-designed guidewires are needed to allow for the safe treatment of total or near-total vessel occlusions. The guidewires should exhibit sufficient stiffness allowing for penetration into hard or calcified tissues or occlusions without kinking and be designed to reduce the risk of vessel wall perforation.

Specially-designed guidewires and related methods allowing for percutaneous crossing of a total or near-total occlusion in a blood vessel are disclosed in this patent document. A guidewire can include a core member and a jacket member. The core member can extend from a proximal end portion to a distal end portion and can include design and material attributes that impart varying flexibility and stiffness characteristics to different portions of the guidewire. The distal end portion can include a first segment, a more distal second segment and a more proximal third segment. The first segment can be designed to encourage predictable, elastic prolapse without kinking during use. The jacket member can surround at least the distal end portion of the core member. A method can include advancing a distal end portion of the guidewire through the natural lumen of a blood vessel to a location near an occlusion. A longitudinal pushing force can be applied to a proximal end portion of the guidewire, thereby causing a first segment of the distal end portion to elastically prolapse. The distal end portion of the guidewire can be advanced through or around the occlusion, led by the prolapsed portion's atraumatic radius of curvature.

To further illustrate the guidewires and methods disclosed herein, a non-limiting list of examples is provided here:

In Example 1, a guidewire can include a core member and a jacket member. The core member can extend from a proximal end portion to a distal end portion with an intermediate portion therebetween. The distal end portion can include a first segment, a more distal second segment and a more proximal third segment. The first segment can be configured to encourage prolapse without kinking. The jacket member can surround at least the distal end portion of the core member.

In Example 2, the guidewire of Example 1 is optionally configured such that the first segment has a short length range of about 0.05 cm to about 1 cm, inclusive.

In Example 3, the guidewire of Example 2 is optionally configured such that the short length of the first segment is in a range of about 0.05 cm to about 0.5 cm, inclusive.

In Example 4, the guidewire of any one or any combination of Examples 2 or 3 is optionally configured such that a diameter of a proximal end of the second segment is at least 40 percent less than a diameter of a distal end of the third segment. The diameter reduction can take place within the first segment and provide focused prolapse of the guidewire's distal end portion.

In Example 5, the guidewire of any one or any combination of Examples 2 or 3 is optionally configured such that a diameter of a proximal end of the second segment is at least 50 percent less than a diameter of a distal end of the third segment. The diameter reduction can take place within the first segment and provide focused prolapse of the guidewire's distal end portion.

In Example 6, the guidewire of any one or any combination of Examples 1-5 is optionally configured such that longitudinal stiffness of the third segment is greater than longitudinal stiffness of the first and second segments.

In Example 7, the guidewire of Example 6 is optionally configured such that longitudinal stiffness of the second segment is greater than longitudinal stiffness of the first segment.

In Example 8, the guidewire of any one or any combination of Examples 1-7 is optionally configured such that the outer surface of the first segment includes a parabolic shape or near-parabolic shape.

In Example 9, the guidewire of Example 8 is optionally configured such that the parabolic or near-parabolic shape defines at least three different radii of curvature.

In Example 10, the guidewire of any one or any combination of Examples 1-7 is optionally configured such that the outer surface of the first segment includes a cylindrical shape having a smaller diameter than the rest of the core member.

In Example 11, the guidewire of Example 10 is optionally configured such that the cylindrical shape is longitudinally bounded by portions of the core member including frustoconical shapes.

In Example 12, the guidewire of any one or any combination of Examples 1-11 is optionally configured such that the first segment, when prolapsed, defines a radius of curvature in a range of about 0.1 cm to about 1.0 cm, inclusive. A radius of curvature in a range of about 0.1 cm to about 0.5 cm can be preferred in some examples.

In Example 13, the guidewire of any one or any combination of Examples 1-12 is optionally configured such that the distal end portion includes a single distal tip.

In Example 14, the guidewire of any one or any combination of Examples 1-12 is optionally configured such that the distal end portion includes two distal tips oriented in opposing directions.

In Example 15, the guidewire of any one or any combination of Examples 1-12 is optionally configured such that the distal end portion includes at least three distal tips oriented in directions equally spaced from one another.

In Example 16, the guidewire of any one or any combination of Examples 13-15 is optionally configured such that at least one distal tip includes a preformed, non-linear configuration.

In Example 17, the guidewire of Example 16 is optionally configured such that the preformed, non-linear configuration includes the first segment and the second segment.

In Example 18, the guidewire of Example 16 is optionally configured such that the preformed, non-linear configuration is a pigtail shape.

In Example 19, the guidewire of Example 16 is optionally configured such that the preformed, non-linear configuration is a "J" shape.

In Example 20, the guidewire of Example 16 is optionally configured such that the preformed, non-linear configuration is a corkscrew shape.

In Example 21, the guidewire of any one or any combination of Examples 1-20 is optionally configured such that the jacket member is a coil.

In Example 22, the guidewire of any one or any combination of Examples 1-20 is optionally configured such that the jacket member is a polymer coating.

In Example 23, the guidewire of Example 22 is optionally configured such that the polymer coating includes a radiopaque material.

In Example 24, the guidewire of any one or any combination of Example 1-23 is optionally configured such that all bonds between the core member and the jacket member exhibit a tensile strength of 0.67 lbs or more.

In Example 25, a method comprises advancing a distal end portion of a guidewire through the natural lumen of a blood vessel to a location near an occlusion; applying a longitudinal force to a proximal end portion of the guidewire, including causing a segment of the distal end portion to prolapse; and further advancing the distal end portion of the guidewire through or around the occlusion, led by the prolapsed segment.

In Example 26, the method of Example 25 is optionally configured such that advancing the distal end portion of the guidewire through the natural lumen of the blood vessel includes advancing a core member with a distal end portion comprising a first segment having a first longitudinal stiffness, a more distal second segment having a second longitudinal stiffness, and a more proximal third segment having a third longitudinal stiffness greater than the first longitudinal stiffness and the second longitudinal stiffness.

In Example 27, the method of Example 26 is optionally configured such that applying the longitudinal force to the proximal end portion of the guidewire includes applying a force greater than the first longitudinal stiffness.

In Example 28, the method of any one or any combination of Examples 25-27 is optionally configured such that advancing the distal end portion of the guidewire through the natural lumen of the blood vessel includes leading with a non-linear distal tip configuration, thereby minimizing the possibility of damaging the blood vessel wall.

In Example 29, the method of any one or any combination of Examples 25-28 is optionally configured such that advancing the distal end portion of the guidewire through the natural lumen of the blood vessel includes advancing a guidewire constrained to a cross-sectional dimension of 0.036 cm (0.014 in) through the natural lumen of the blood vessel.

In Example 30, the method of Example 29 is optionally configured such that causing the segment of the distal end portion to prolapse includes increasing the cross-sectional constraint of the guidewire to more than 0.036 cm (0.014 in).

In Example 31, the method of any one or any combination of Examples 25-30 is optionally configured such that further advancing the distal end portion of the guidewire through or around the occlusion includes advancing the distal end portion between an intimal layer and an adventitial layer of the blood vessel wall at a location near the occlusion.

In Example 32, the method of any one or any combination of Examples 25-30 is optionally configured such that further advancing the distal end portion of the guidewire through or around the occlusion includes advancing the distal end portion into the occlusion.

In Example 33, the method of any one or any combination of Examples 25-32 optionally further comprises advancing the distal end of a catheter over the guidewire to a location near the distal end portion of the guidewire.

In Example 34, the guidewire or method of any one or any combination of Examples 1-33 can optionally be configured such that all features, components, operations, or other options recited are available to use or select from.

These and other examples and features of the present guidewires and methods will be set forth, at least in part, in the following Detailed Description. This Overview is intended to provide non-limiting examples of the present subject matter—it is not intended to provide an exclusive or exhaustive explanation. The Detailed Description below is included to provide further information about the present guidewires and methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

FIGS. 21-22 illustrate side views of a distal end portion of two guidewire embodiments, with prolapsed configurations shown in phantom.

Figure 1:
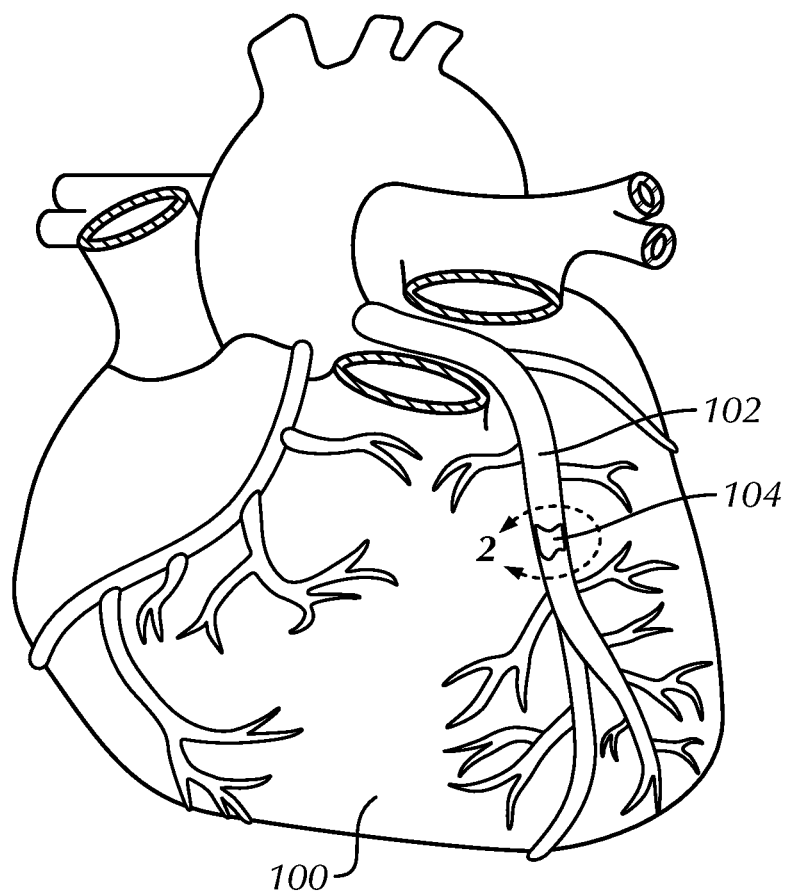
FIG. 1 illustrates a schematic view of a heart, including a coronary artery containing an occlusion.

The drawing figures are not necessarily to scale. Certain features and components may be shown exaggerated in scale or in schematic form and some details may not be shown in the interest of clarity and conciseness.

DETAILED DESCRIPTION

The present subject matter provides guidewires and related methods for crossing or bypassing total or near total occlusions contained in a natural vessel lumen with diminished risk of vessel wall perforation and without guidewire kinking or other plastic deformation. The guidewire can include a core member and a surrounding jacket member. The core member can longitudinally extend from a proximal end portion to a distal end portion and can include design and material attributes that impart varying flexibility and stiffness characteristics to different portions of the guidewire. The distal end portion can include a first segment, a more distal second segment and a more proximal third segment. The first segment can include a short taper or a diameter-reduced portion to encourage focused, predictable, elastic prolapse without direct inducement from a treating clinician. The distal end portion, when prolapsed, can inhibit unintended vessel wall perforation when crossing or bypassing vessel occlusions. The prolapsed portion can be integrated into a non-linear, preformed distal tip or formed during use in response to a proximally-applied pushing force and can provide an effective atraumatic tip that can distribute any pushing forces from a treating clinician to a relatively large tissue or occlusion surface area.

While the present guidewires and methods will primarily be discussed in relation to treatment of coronary arteries, they may also be useful in other blood vessels including peripheral arteries and veins for the treatment of peripheral vascular diseases and arterio-venous grafts, for example.

FIG. 1 illustrates a schematic view of a heart 100, including a coronary artery 102 containing an occlusion 104. As used herein, an "occlusion" may be a total (e.g., a CTO), near total or partial blockage of a blood vessel.

Figure 2:
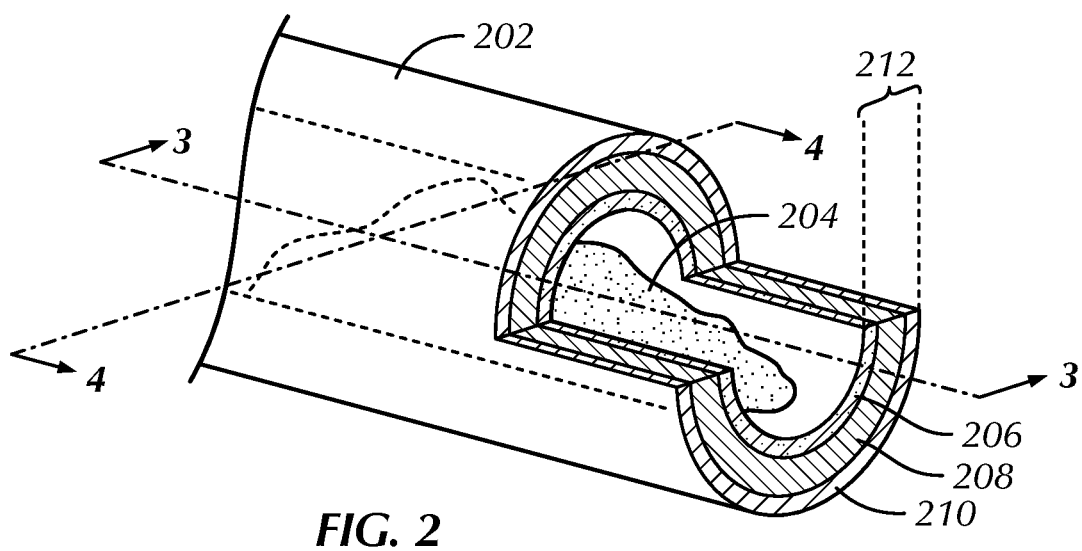
FIG. 2 illustrates a schematic view of a coronary artery containing an occlusion and the artery's intimal, medial and adventitial wall layers.

FIG. 2 illustrates a schematic view of a coronary artery 202 containing an occlusion 204. The coronary artery's wall 212 includes intimal 206, medial 208 and adventitial 210 layers. Concentrically outward of the intima 206 is the medial layer 208. The transition between the external most portions of the intima 206 and the internal most portions of the medial 208 can be referred to as the subintimal region. The outermost layer of the artery is the adventitia 210.

The anatomy of a venous wall is similar to the anatomy of an arterial wall with two primary exceptions. First, arterial walls are thicker than venous walls to withstand higher pressures produced from heartbeats. Second, an endothelium layer on an inner surface of the intima of a vein includes one or more valves. Since blood in veins flows against gravity, the valves prevent backflow and keep blood moving toward the heart. The similarities between venous and arterial wall anatomies allow the present guidewires and methods to be used in a similar manner in both vessel types.

Figure 3:
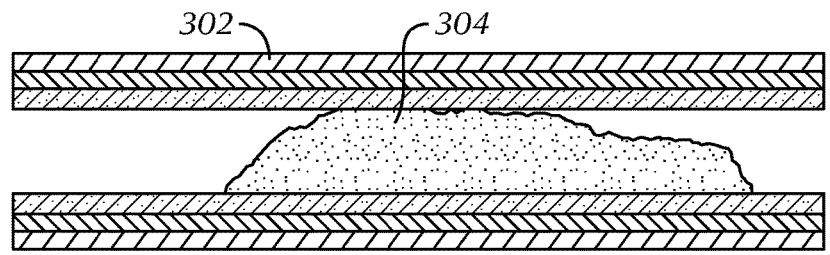
FIG. 3 illustrates a longitudinal cross-section of a coronary artery containing an occlusion, such as a cross-section taken along line 3-3 of FIG. 2.
Figure 4:
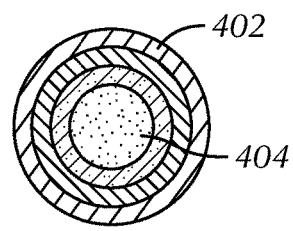
FIG. 4 illustrates a transverse cross-section of a coronary artery containing an occlusion, such as a cross-section taken along line 4-4 of FIG. 2.

FIGS. 3 and 4 illustrate cross-sections of a coronary artery 302, 402 containing an occlusion 304, 404 in the form of a CTO. FIG. 3 is a longitudinal cross-section taken along line 3-3 of FIG. 2. FIG. 4 is a transverse cross-section taken along line 4-4 of FIG. 2. It is believed that the present guidewires and related methods can find utility in the successful treatment of CTOs or near total blockages of blood vessels.

Figure 5:
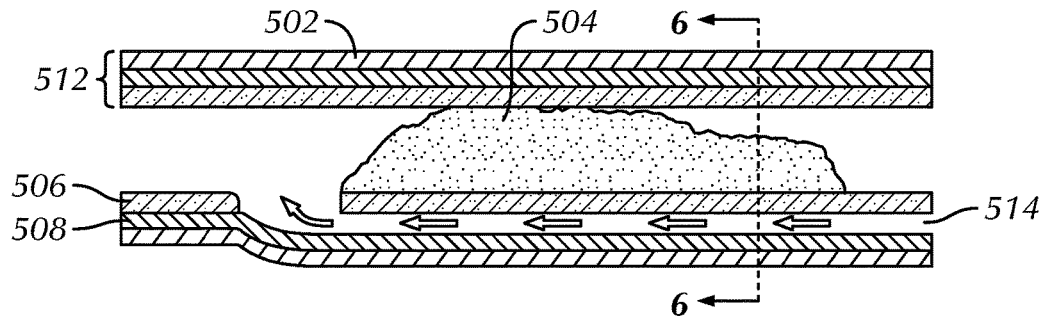
FIG. 5 illustrates a schematic view, in longitudinal cross-section, of a subintimal track around an occlusion, with reentry into the natural blood vessel lumen at a location distal of the occlusion.

FIG. 5 illustrates a schematic view, in longitudinal cross-section, of a subintimal track 514 established around an occlusion 504 within a coronary artery 502. Using a minimally invasive guidewire technique, a subintimal track 514 can be created between the external most portions of the intimal layer 506 and the internal most portions of the medial layer 508 of the arterial wall 512. The track 514 can reenter the natural lumen of the artery 502 at a location distal of the occlusion 504.

Figure 6:
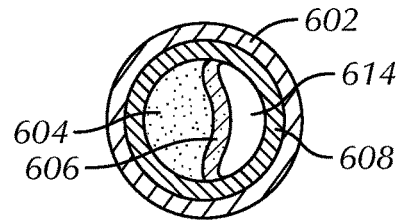
FIG. 6 illustrates a transverse cross-section of a coronary artery containing an occlusion and a subintimal track around the occlusion, such as a cross-section taken along line 6-6 of FIG. 5.

FIG. 6 is a transverse cross-section taken along line 6-6 of FIG. 5 and illustrates a subintimal track 614 created around an occlusion 604 within a coronary artery 602. The subintimal track 614 is shown between the external most portions of the intimal layer 606 and the internal most portions of the medial layer 608.

The term "guidewire" as used herein is to be broadly construed to include wire-like structures of dimension and length that are intended to safely navigate through or around an occlusion in a blood vessel. The guidewires can include a core member having design and material attributes that impart varying flexibility and stiffness characteristics to different portions of the guidewire. The wire-like structures can include, but are not limited to, diagnostic, therapeutic or interventional guidewires, wire guides, spring wires, exchange guidewires and extension wires. Transverse dimensions of the guidewires can primarily fall in the range of about 0.025 cm (0.010 in) to about 0.036 cm (0.014 in) in diameter and about 30 cm to about 300 cm (or more) in length. The guidewires can be coated or treated with various compositions (e.g., polymers or other compounds) to change their handling or performance characteristics, such as to increase lubricity, to increase or decrease hydrophobicity, or to reduce thrombogenicity of portions of their external surface. A hydrophilic polymer in the form of polyvinylpyrrolidone, for example, can exhibit lubricity when moistened. A polymer in the form of polytetrafluoroethylene (PTFE) can reduce the coefficient of friction. The guidewires can also remain uncoated and untreated.

Figure 7:
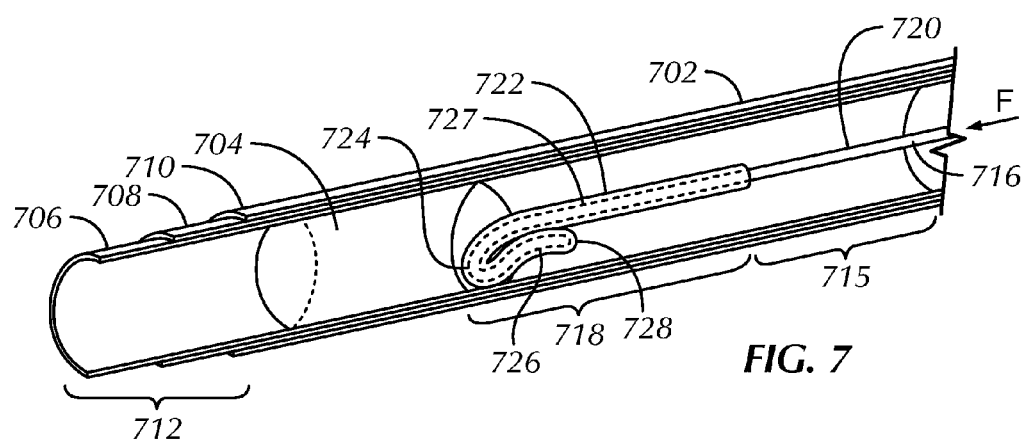
FIG. 7 illustrates an isometric view of a coronary artery containing an occlusion and a guidewire, as constructed in accordance with at least one embodiment, advanced against a proximal side of the occlusion and a portion of the adjacent arterial wall.

FIG. 7 illustrates an isometric view of a coronary artery 702 containing an occlusion 704 (shown to be cylindrical in shape for clarity) and a distal end portion 718 of a guidewire 716. The distal end portion 718 has been navigated through the artery 702 to a location near the occlusion 704.

The guidewire 716 can extend from a proximal end portion to the distal end portion 718 and can include an intermediate portion 715 therebetween. The guidewire 716 can include a core member 720 and a jacket member 722. The core member 720, at the guidewire's distal end portion 718, can include a first segment 724, a more distal second segment 726 and a more proximal third segment 727. The jacket member 722 can surround at least the first 724, second 726 and third 727 segments of the core member 720 and can have a length of about 6 cm to 12 cm. In an example, the jacket member 722 is a coil. In an example, the jacket member 722 is a polymer coating optionally including a radiopaque material. Bonds between the jacket member 722 and the core member 720 can exhibit a tensile strength of 0.67 lbs or more.

As discussed further below, particularly in association with FIGS. 14-16, the first segment 724 of the core member 720 can include a short taper or a diameter-reduced portion to encourage focused, predictable prolapse. The first segment 724, due to the short taper or diameter-reduced portion, can have a longitudinal stiffness less than the longitudinal stiffness of the second segment 726 and the longitudinal stiffness of the third segment 727 of the core member 720. Prolapse can be integrated into a non-linear, preformed distal tip 728 of the guidewire 716, as shown in FIGS. 17-20, or can occur when the tip 728 contacts the occlusion 704 or an adjacent arterial wall portion 712 while a proximally-initiated pushing force F, having a magnitude greater than the stiffness of the first segment 724, is applied by the treating clinician at the proximal end portion as shown in FIGS. 7, 21 and 22. The amount of force F needed for the distal end portion 718 to prolapse in the examples of FIGS. 7, 21 and 22 can be comparatively small, thereby preventing kinking of the remaining portions of the guidewire 716 as it is advanced distally through the coronary artery 702.

Led by the prolapsed first segment 724 and the surrounding jacket member 722, the guidewire 716 can be safely pushed through the occlusion 704 or steered around the occlusion 704 by way of the arterial wall 712. The prolapsed first segment 724 can create a space or track of adequate size for a later-inserted treatment device.

Figure 8:
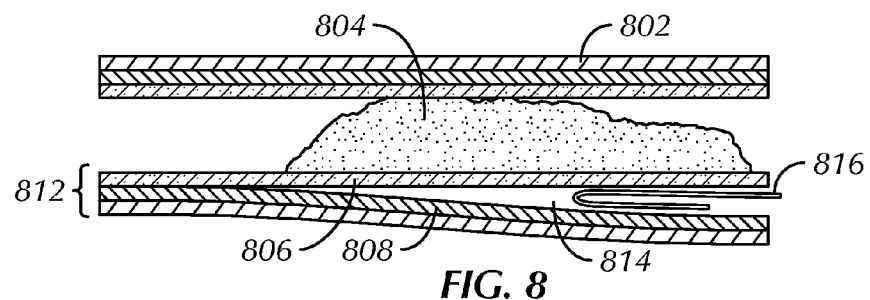
FIGS. 8-10 illustrate longitudinal cross-sections of a coronary artery containing an occlusion and a subintimal track around the occlusion being established by a guidewire including a prolapsable distal end portion, as constructed in accordance with at least one embodiment.
Figure 9:
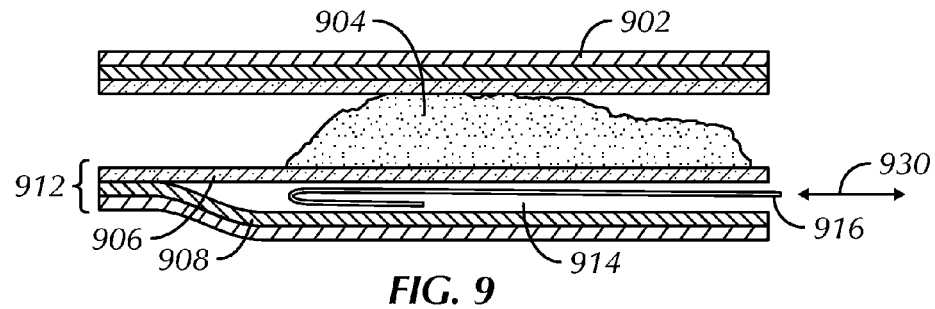
Figure 10:
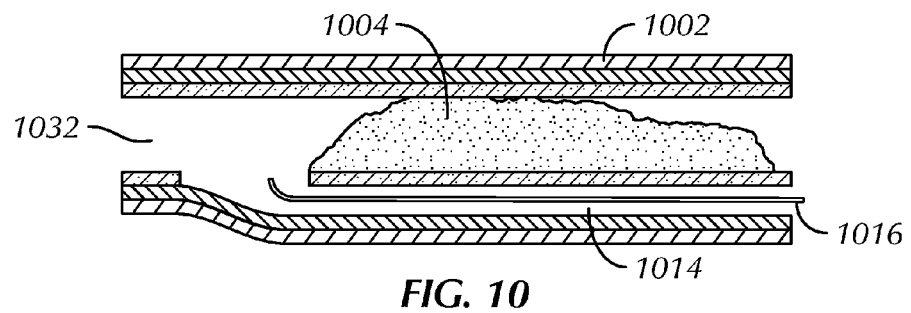

FIGS. 8-10 illustrate sequential cross-sectional views of a coronary artery 802, 902, 1002 containing an occlusion 804, 904, 1004 and a subintimal track 814, 914, 1014 created around the occlusion by a guidewire 816, 916, 1016 and, more specifically, a prolapsed segment of the guidewire. In FIG. 8, the guidewire 816 has been pushed into position between the external most portions of the intimal layer 806 and the internal most portions of the medial layer 808 of the arterial wall 812. As the guidewire 916 is further advanced by a proximally-applied force, a delamination plane 930 between the intimal 906 and medial layers 908 is created around the occlusion 904, as shown in FIG. 9. The curvature of the prolapsed segment helps to minimize the possibility of penetrating the arterial wall 912 as the guidewire continues around the occlusion 904 and eventually rejoins with the natural lumen 1032 of the coronary artery 1002, as shown in FIG. 10.

Figure 11:
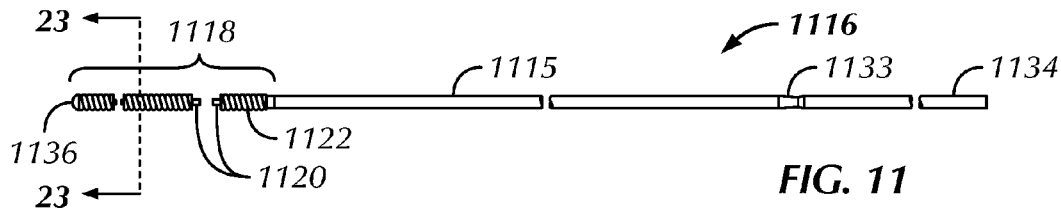
FIG. 11 illustrates an elevational side view of a guidewire, as constructed in accordance with at least one embodiment.

FIG. 11 illustrates an elevation side view of a guidewire 1116, as constructed in accordance with at least one embodiment. The guidewire 1116 can extend from a proximal end portion 1134, intended to remain outside of the subject for manipulation by a treating clinician, to an intermediate portion 1115 and a distal end portion 1118, intended to be inserted into a blood vessel of the treated subject. The guidewire 1116 can include a core member 1120 and a jacket member 1122, which can influence the behavior and characteristics of the guidewire.

The core member 1120 can be made of the same material along its length or, in some embodiments, can include portions or segments made of different materials. The material(s) used to construct the core member 1120 can be chosen to help the member's size and shape impart varying flexibility and stiffness characteristics to different portions of the core member. By way of example, the proximal and distal end portions of the core member 1120 can be formed of different materials, such as materials having different moduli of elasticity resulting in a difference in flexibility, and can be coupled at a segment 1133 of the core member 1120 having a parabolic or near-parabolic grind. The material (e.g., stainless steel) used to construct the proximal end portion can be relatively stiff for pushability and torqueability, and the material (e.g., nickel-titanium (NiTi)) used to construct the distal end portion can be relatively flexible by comparison for better lateral trackability and steerability. Material options for the core member 1120 can include metals (e.g., stainless steel), metal alloys (e.g., NiTi), polymers and metal-polymer composites.

Figure 12:
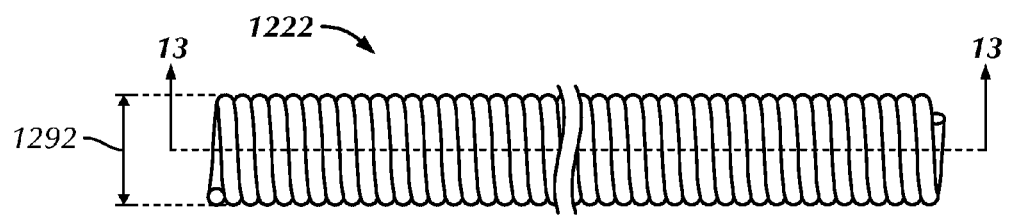
FIGS. 12-13 illustrate side and longitudinal cross-section views, respectively, of a jacket member in the form of a coil, as constructed in accordance with at least one embodiment.
Figure 13:
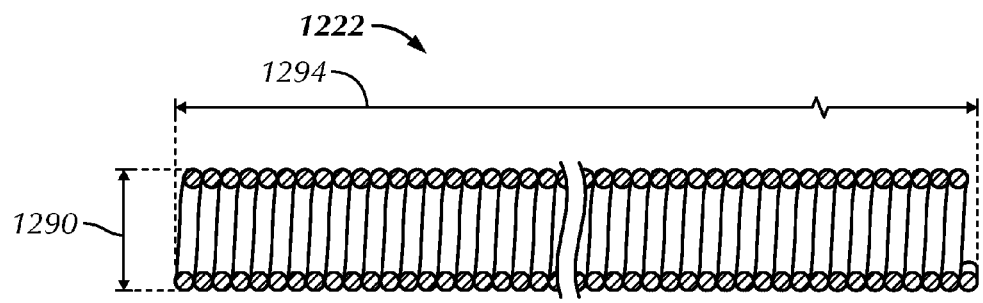

The jacket member 1122 can include a flexible helical coil attached to, and extending about, the distal end portion of the core member 1120. The coil can be formed from a suitable highly radiopaque alloy such as a gold-platinum, platinum-coated tungsten or gold-coated tungsten alloy. The coil can be formed from wire on the order of 0.003 cm (0.0010 in) to 0.008 cm (0.0030 in) in outer dimension and have a circular, rectangular or square cross-sectional configuration. Adjacent turns of the coil can be in spaced relation, in contact, or loosely interlocked with each other. In the example of FIGS. 12 and 13, the jacket member 1222 is formed from a coiled wire having a diameter of 0.004 cm to 0.005 cm, with adjacent turns of the wire having a 5 percent pitch. The jacket member 1222 can include an inner diameter 1290 in a range of about 0.010 cm to 0.030 cm, an outer diameter 1292 in a range of about 0.020 cm to 0.036 cm, and a length 1294 in a range of about 6 cm to 20 cm.

Referring again to FIG. 11, a head plug member 1136 can optionally be provided at, and welded to, the distal end tip of the core member 1120 or the jacket member 1122.

In at least some embodiments, portions or all of the core member 1120, the jacket member 1122 or the head plug member 1136 can be doped with, made of or otherwise include a radiopaque material. Radiopaque materials are capable of producing a relatively bright image on a fluoroscopy screen or other imaging display during a medical procedure. This relatively bright image aids the treating clinician of the guidewire 1116 in determining its location at a desired instant. Some examples of radiopaque materials can include, but are not limited to, gold, platinum, palladium, tantalum, tungsten alloy, polymer material loaded with radiopaque filler, and the like. Additionally, other radiopaque marker bands or coils can also be incorporated into the design of the guidewire 1116 to achieve the same or similar result.

In some embodiments, a degree of Magnetic Resonance Imaging (MRI) compatibility is imparted into the guidewire 1116 to enhance compatibility with MRI machines. For example, the core member 1120, the jacket member 1122, the head plug member 1136 or portions thereof, can be made of a material that does not substantially distort the guidewire image or create substantial artifacts (or gaps) in the guidewire image. The core member 1120, the jacket member 1122, the head plug member 1136 or portions thereof can be made from a material that the MRI machine can image, such as tungsten, cobalt-chromium-molybdenum alloys, nickel-cobalt-chromium-molybdenum alloys, nitinol and the like.

The distal end portion 1118 of the guidewire 1116 should allow a treating clinician to steer the structure through the branches of a subject's blood vessels and manipulate it to a diseased site in an intended vessel. Additionally, the distal end portion 1118 should be sufficiently flexible to pass through sharply curved tortuous coronary anatomy, as well as to provide a sufficiently soft leading tip that will not injure vessel wall tissue during use. Further, the guidewire should have sufficient column strength so that it can be pushed without kinking. A configuration of the core member 1120, such as the configurations discussed below, can impart certain advantageous flexibility and stiffness characteristics to the guidewire 1116.

Figure 14:
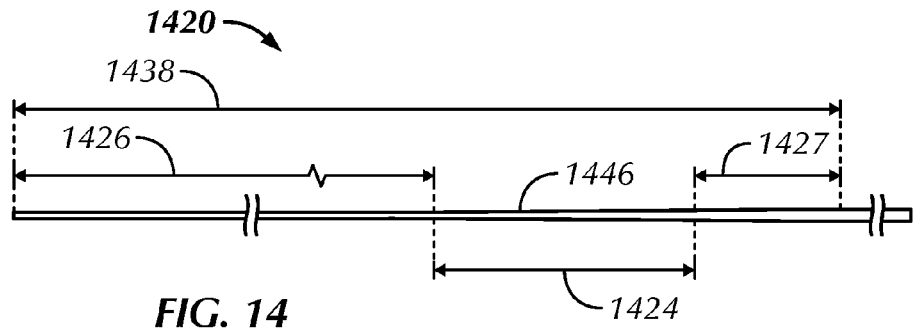
FIGS. 14-16 illustrate side views of a distal end portion of various core member embodiments in a non-prolapsed configuration and having a straightened or unbiased distal tip.
Figure 15:
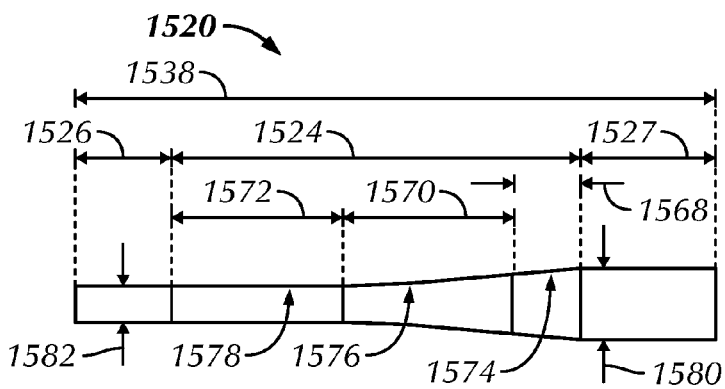
Figure 16:
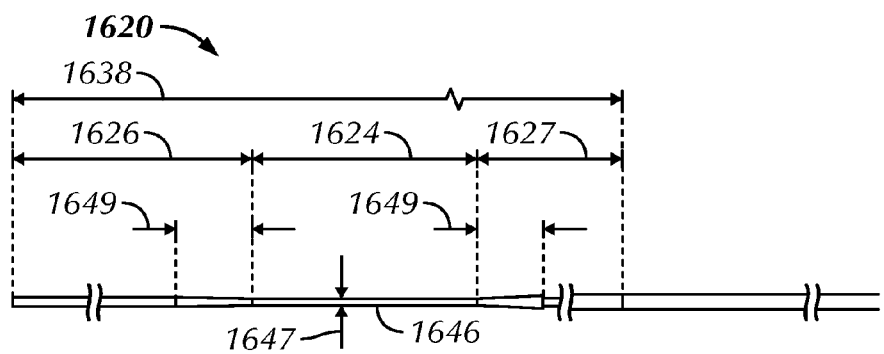

FIGS. 14, 15 and 16 illustrate side views of a distal end portion 1438, 1538, 1638 of various core member embodiments 1420, 1520, 1620 in a non-prolapsed configuration and with a straightened or unbiased distal tip. A distal end portion 1438, 1538, 1638 of each core member 1420, 1520, 1620 can include at least first 1424, 1524, 1624, second 1426, 1526, 1626, and third 1427, 1527, 1627 segments. The first segment 1424, 1524, 1624 can be located proximally of the second segment 1426, 1526, 1626 and distally of the third segment 1427, 1527, 1627, and can be spaced between about 0.5 cm and about 6 cm, inclusive, from a distal tip of the core member 1420, 1520, 1620. The first segment 1424, 1524, 1624 can be the most flexible (least stiff) portion of the core members 1420, 1520, 1620 and can encourage prolapse. By way of example, the first segment 1424, 1524, 1624 can have a stiffness level in the range of about 0.2 g to about 6 g, inclusive, and the second segment 1426, 1526, 1626 and/or the third segment 1427, 1527, 1627 can have a stiffness level in the range of about 8 g to about 30 g, inclusive. In various examples, the third segment 1427, 1527, 1627 has a stiffness level greater than the stiffness level of the first and second segments, such as a stiffness level greater than about 15 g.

As shown in FIGS. 14 and 15, the distal end portion 1438, 1538 of the core member 1420, 1520 can be generally tapered and its first segment 1424, 1524 can have an outer surface 1446, 1546 including a continuously tapering shape. The first segment 1424, 1524 can be a short parabolic or near-parabolic shape. The parabolic or near-parabolic shape can include at least three portions 1568, 1570, 1572 having a short combined length in a range of about 0.05 cm to about 1 cm, inclusive, with each portion defining a different radius of curvature 1574, 1576, 1578 such as 0.382 cm (0.1504 in), 0.764 cm (0.3008 in) and 1.528 cm (0.6016 in), respectively. The parabolic or near-parabolic shape can taper in diameter 40 percent or more along its length to induce prolapse, such as from a proximal diameter 1580 of about 0.015 cm (0.0060 in) or 0.020 cm (0.0080 in) to a distal diameter 1582 of about 0.008 cm (0.0030 in) or less along a preferred length of about 0.05 cm to about 0.5 cm, inclusive. This short length of taper can focus the location of encouraged prolapse along the length of the associated guidewire.

As shown in FIG. 16, the distal end portion 1638 of the core member 1620 can include a first segment 1624 having a cylindrical outer surface 1646, a length of in the range of about 0.1 cm to about 1 cm, inclusive, and a diameter 1647 smaller than the rest of the core member. In an example, the diameter 1647 is in the range of 0.005 cm (0.0020 in) to 0.009 cm (0.0035 in), inclusive, such as about 0.008 cm (0.0030 in), while a third segment 1627 proximal of the first segment 1624 includes a diameter of about 0.020 cm (0.0080 in) and a second segment 1626 distal of the first segment 1624 includes a diameter of about 0.010 cm (0.0040 in) or more. The first segment 1624 can be longitudinally bounded by portions 1649 of the core member 1620 including frusto-conical shapes, which have a length in the range of about 0.05 cm to about 0.2 cm, inclusive.

FIGS. 17-20 illustrate side views of a distal end portion 1718, 1818, 1918, 2018 of guidewire embodiments 1716, 1816, 1916, 2016 including one or more prolapsed segments 1725, 1825, 1925, 2025 integrated into one or more non-linear, preformed distal tips 1728, 1828, 1928, 2028. Each segment 1725, 1825, 1925, 2025 can help encourage the non-linear configurations of the distal tips 1728, 1828, 1928, 2028 and can inhibit further prolapse of the guidewire 1716, 1816, 1916, 2016 as it is advanced through or around an occlusion by the treating clinician.

FIGS. 21 and 22 illustrate side views of a distal end portion 2118, 2218 of guidewire embodiments 2116, 2216 including a prolapsable segment 2125, 2225 spaced from a distal tip 2128, 2228. To avoid harming vessel wall tissue during a procedure, the prolapsable segment 2125, 2225 of the guidewire 2116, 2216 can prolapse and allow the distal tip 2128, 2228 to be oriented in a direction opposite or nearly opposite advancement of the guidewire. Following prolapse, advancement of the guidewire 2116, 2216 is led by a relatively large, flexible radius of curvature 2144, 2244 providing an atraumatic surface. The height 2164, 2264 of the prolapsed portion can range from about 1 cm to about 6 cm, inclusive, such as about 2 cm, 3 cm or 4 cm.

The distal end portion 1718, 1818, 1918, 2018, 2118, 2218 of each guidewire 1716, 1816, 1916, 2016, 2116, 2216, respectively shown in FIGS. 17-22, can be divided into segments corresponding to segments of an included core member (e.g., core member 1420, 1520, 1620 of FIGS. 14-16). The guidewires 1716, 1816, 1916, 2016, 2116, 2216, and more specifically the distal end portions 1718, 1818, 1918, 2018, 2118, 2218 of such guidewires, can include the segment 1725, 1825, 1925, 2025, 2125, 2225 encouraging predictable prolapse. A segment of the core member (e.g., the first segment 1424, 1524, 1624 of core members 1420, 1520, 1620) can impart prolapse characteristics to the prolapse guidewire segment 1725, 1825, 1925, 2025, 2125, 2225.

The distal end portion 1718, 1818, 1918, 2018, 2118, 2218 of each guidewire 1716, 1816, 1916, 2016, 2116, 2216 can have a length ranging from about 5 cm to about 50 cm, such as about 6 cm, 8 cm, 9 cm or 10 cm. By providing a distal end portion 1718, 1818, 1918, 2018, 2118, 2218 that encourages predictable prolapse and is free of shoulders or other stress risers, the guidewires 1716, 1816, 1916, 2016, 2116, 2216 can navigate through or around an occlusion safely without kinking and provide responsive steerability. Additionally, the guidewires 1716, 1816, 1916, 2016, 2116, 2216 can be designed with sufficient column strength (or stiffness) along their lengths to help advance the prolapsed distal portion beyond the occlusion by transmitting the necessary force from a proximal end portion to the distal end portion 1718, 1818, 1918, 2018, 2118, 2218.

Figure 17:
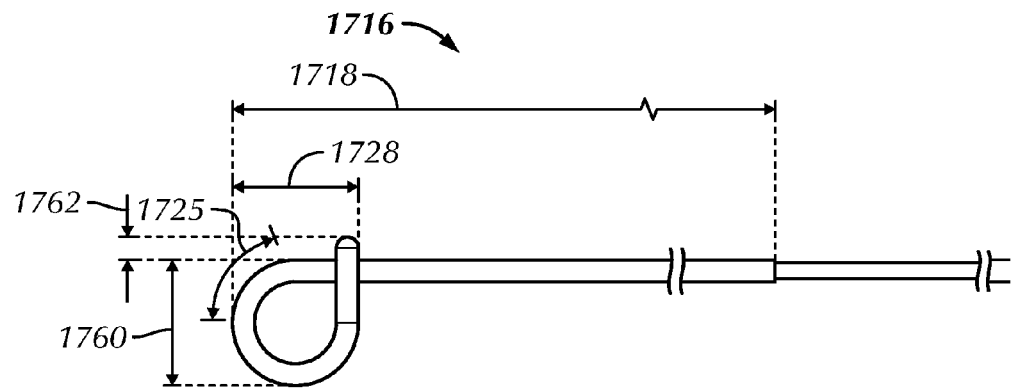
FIGS. 17-20 illustrate side views of a distal end portion of various guidewire embodiments, with prolapsed configurations integrated into one or more non-linear, preformed distal tips.
Figure 18:
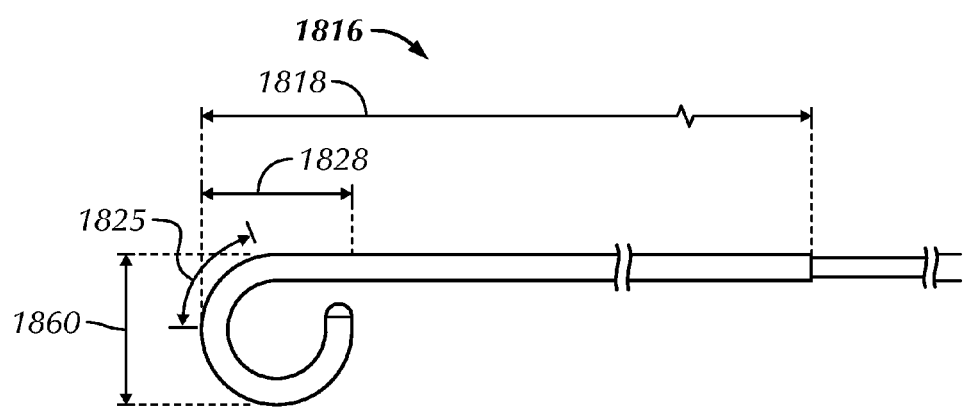
Figure 19:
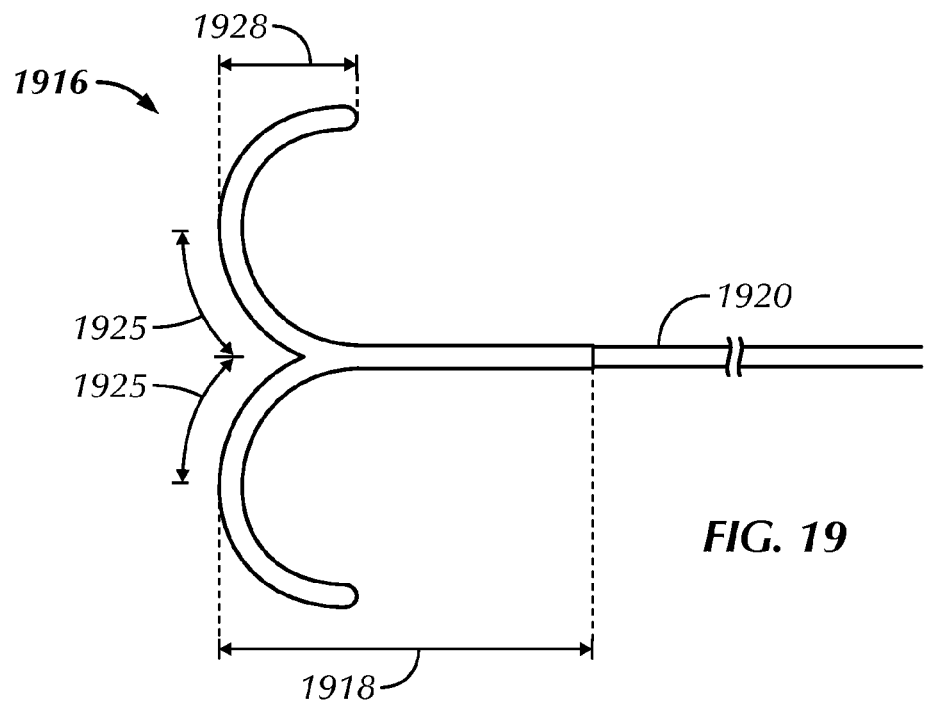
Figure 20:
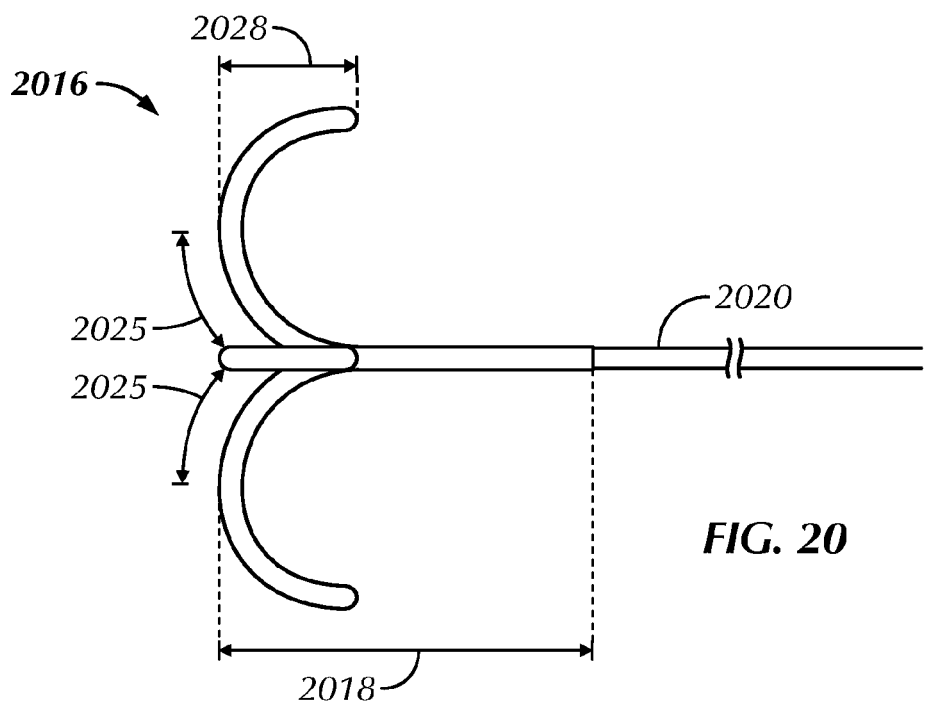

The guidewires 1716, 1816, 1916, 2016, 2116, 2216 can include a single distal tip 1728, 1828, 2128, 2228, as shown in FIGS. 17, 18, 21 and 22, or multiple distal tips 1928, 2028, as shown in FIGS. 19 and 20. Each distal tip can include a preformed, non-linear configuration, such as the pigtail shape shown in FIGS. 17 and 18, the "J" shape shown in FIGS. 19 and 20 or the corkscrew shape shown in FIG. 22. Each distal tip can alternatively include a linear configuration, as shown in FIG. 21. In the example of FIG. 17, the tip 1728 of the pigtail shape can overlap the longitudinal axis of the guidewire 1716 by a predefined amount 1762, such as about 0.02 cm to about 0.05 cm. The height 1760, 1860 of the pigtail shape can range from about 0.1 cm to about 0.3 cm, as shown in FIGS. 17 and 18. The pigtail or other curved shape can assist with preventing damage to vessel wall tissue as a guidewire is advanced within the treated subject. The corkscrew shape of FIG. 22 can help propel the guidewire through a desired vessel when rotated. The height 2284 of the corkscrew can range from about 0.1 cm to about 0.4 cm, such as about 0.17 cm. The multiple distal tips 1928, 2028 of the guidewires 1916, 2016 shown in FIGS. 19 and 20 can be equally spaced about a core wire 1920, 2020 such that the guidewire maintains a balanced feel during use. The two distal tips 1928 of FIG. 19 can be spaced about 180 degrees from each other and the three distal tips 2028 of FIG. 20 can be spaced about 120 degrees from each other.

Figure 23:
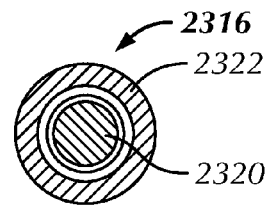
FIG. 23 illustrates a transverse cross-section of a guidewire, as constructed in accordance with at least one embodiment, such as along line 23-23 of FIG. 11.

FIG. 23 illustrates a transverse cross-section of a guidewire 2316, such as along line 23-23 of FIG. 11. The guidewire 2316 can include a core member 2320 and a jacket member 2322. The circular cross-sectional shape of the core member 2320 can allow the guidewire's 2316 distal end portion to be isotropic in bending and prolapse in any plane with approximately equal stress and strain. Additionally, the circular cross-sectional shape of the core member 2320 can reduce or eliminate the whipping movements found to exist when urging rotation of guidewires having a rectangular and other non-circular cross-section.

Figure 24:
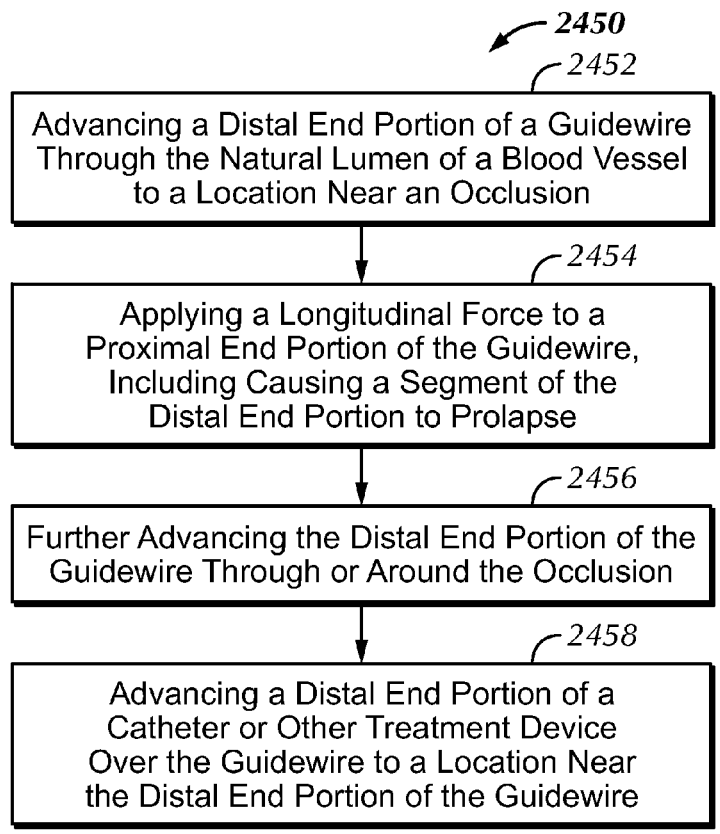
FIG. 24 illustrates a method of using a guidewire to navigate through or around an occlusion, as constructed in accordance with at least one embodiment.

FIG. 24 illustrates a method 2450 of using a guidewire to navigate through or around an occlusion. In operation 2452, the method can include advancing a distal end portion of the guidewire through the natural lumen of a blood vessel to a location near an occlusion. The distal end portion of the guidewire can include a core member having a distal end portion comprising a first segment, a more distal second segment and a more proximal third segment. The distal tip of the second segment can optionally include a non-linear, preformed configuration to minimize the possibility of penetrating the blood vessel wall during initial advancement of the guidewire within the vessel.

A longitudinal pushing force can be applied by a treating clinician to a proximal end portion of the guidewire in operation 2454, thereby causing the first segment of the core member and the guidewire's distal end portion to prolapse. The pushing force can have a longitudinal magnitude greater than the longitudinal stiffness of the first segment.

With the distal end portion prolapsed, the guidewire can be further advanced in operation 2456 through or around the occlusion by the treating clinician, led by the prolapsed segment. In some examples, the distal end portion of the guidewire can be advanced between an intimal layer and an adventitial layer of the blood vessel wall starting at a location near the occlusion. In other examples, the distal end portion of the guidewire can be advanced into and through the occlusion, remaining in the natural lumen of the vessel throughout the procedure.

In operation 2458, the method can include advancing the distal end of a catheter or other treatment device over the guidewire to a location near the distal end portion of the guidewire. The catheter or other treatment device can cross the occlusion using the guidewire as a rail and subsequently be used to perform balloon angioplasty, stenting, atherectomy or another endovascular treatment method for opening the occlusion.

Closing Notes:

Cardiovascular disease, including atherosclerosis, is a leading cause of death in the United States and elsewhere. A method for treating atherosclerosis and other forms of vessel lumen narrowing is angioplasty. The objective of angioplasty is to restore adequate blood flow through the affected vessel and can be accomplished by introducing a guidewire through or around a diseased (occlusion) site and then threading a catheter or other treatment device over the guidewire rail. At the diseased site, the catheter or other treatment device can restore blood flow through the vessel by removing, dilating or otherwise opening any occlusions.

The present guidewires and related methods allow for penetration into or around hard or calcified tissues or occlusions with reduced risk of both vessel wall perforation and guidewire kinking. The guidewires can include a distal end portion having a segment configured to encourage predictable, elastic prolapse without the treating clinician having to directly induce such shape formation. The prolapsed portion can be influenced by a core member construction including a short taper or a diameter-reduced portion and can be integrated into a non-linear, preformed distal tip or formed during use in response to a proximally-applied pushing force. It is believed that the distal end portion of the present guidewires provides an advantageous combination of properties including flexibility, stiffness, force transmission, steerability, and an atraumatic prolapsable tip that distributes proximally-initiated pushing forces from a treating clinician to a relatively large tissue or occlusion surface area. Initial testing has found that the distal end portion of the present guidewires can be predictably prolapsed and advanced through or around vessel obstructions without guidewire kinking.

The above Detailed Description includes references to the accompanying drawings, which form a part of the Detailed Description. The Detailed Description should be read with reference to the drawings. The drawings show, by way of illustration, specific embodiments in which the present guidewires and methods can be practiced. These embodiments are also referred to herein as "examples."

The above Detailed Description is intended to be illustrative, and not restrictive. For example, the above-described examples (or one or more features or components thereof) can be used in combination with each other. Other embodiments can be used, such as by one of ordinary skill in the art upon reviewing the above Detailed Description. Also, various features or components can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Certain terms are used throughout this patent document to refer to particular features or components. As one skilled in the art will appreciate, different persons may refer to the same feature or component by different names. This patent document does not intend to distinguish between components or features that differ in name but not in function.

For the following defined terms, certain definitions shall be applied, unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" or "distally" refer to a position that is distant from, or in a direction away from, the treating clinician. "Proximal" and "proximally" refer to a position that is near, or in a direction toward, the treating clinician.

In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A method, comprising:
   advancing a distal end portion of a guidewire through the natural lumen of a blood vessel to a location near an occlusion, including advancing a core member with a distal end portion comprising a first segment having a first longitudinal stiffness and a second segment more distal than the first segment and having a second longitudinal stiffness greater than the first longitudinal stiffness;
   applying a longitudinal force greater than the first longitudinal stiffness to a proximal end portion of the guidewire, including causing the first segment of the distal end portion to prolapse, wherein the first segment has a length in a range of 0.05 cm to 1 cm, inclusive, and the first longitudinal stiffness ranges from 0.2 g to 6 g, inclusive; and
   further advancing the distal end portion of the guidewire through or around the occlusion, led by the prolapsed segment.

2. The method of claim 1, wherein advancing the distal end portion of the guidewire through the natural lumen of the blood vessel further includes advancing a core member with a distal end portion comprising a third segment more proximal than the first segment and having a third longitudinal stiffness greater than the first longitudinal stiffness and the second longitudinal stiffness.

3. The method of claim 1, wherein advancing the distal end portion of the guidewire through the natural lumen of the blood vessel includes leading with a non-linear distal tip configuration.

4. The method of claim 1, wherein advancing the distal end portion of the guidewire through the natural lumen of the blood vessel includes advancing a guidewire constrained to a cross-sectional dimension of 0.036 cm through the natural lumen of the blood vessel.

5. The method of claim 4, wherein causing the segment of the distal end portion to prolapse includes increasing the cross-sectional constraint of the guidewire to more than 0.036 cm.

6. The method of claim 1, wherein further advancing the distal end portion of the guidewire through or around the occlusion includes advancing the distal end portion between an intimal layer and an adventitial layer of the blood vessel wall at a location near the occlusion.

7. The method of claim 1, wherein further advancing the distal end portion of the guidewire through or around the occlusion includes advancing the distal end portion into the occlusion.

* * * * *